United States Patent
Ryu et al.

(10) Patent No.: US 7,196,035 B2
(45) Date of Patent: Mar. 27, 2007

(54) NI HYDROGENATION CATALYSTS, MANUFACTURE AND USE

(75) Inventors: J. Yong Ryu, League City, TX (US); Hugh M. Putman, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 11/249,867

(22) Filed: Oct. 13, 2005

(65) Prior Publication Data

US 2006/0030482 A1    Feb. 9, 2006

Related U.S. Application Data

(63) Continuation of application No. 10/633,867, filed on Aug. 4, 2003, now Pat. No. 7,022,645.

(51) Int. Cl.
*B01J 23/755* (2006.01)

(52) U.S. Cl. ........................ 502/325; 502/337

(58) Field of Classification Search ............... 502/325, 502/337
See application file for complete search history.

(56) References Cited

U.S. PATENT DOCUMENTS

| 2,620,314 | A | 12/1952 | Hockstra | 252/448 |
|---|---|---|---|---|
| 3,878,259 | A | 4/1975 | Hockele et al. | 585/267 |
| 4,123,462 | A | 10/1978 | Best | 564/480 |
| 4,179,408 | A | 12/1979 | Sanchez et al. | 252/448 |
| 4,273,735 | A | 6/1981 | Jacques et al. | 264/5 |
| 4,581,343 | A | 4/1986 | Blanchard et al. | 502/241 |
| 5,223,472 | A | 6/1993 | Simpson et al. | 502/314 |
| 5,648,312 | A | 7/1997 | Rivas et al. | 502/325 |
| 5,962,367 | A | 10/1999 | Shen et al. | 502/439 |
| 6,207,611 | B1 | 3/2001 | Sun et al. | 502/325 |
| 6,399,538 | B1 | 6/2002 | Hucul | 502/325 |
| 6,576,588 | B2 | 6/2003 | Ryu et al. | 502/331 |
| 6,706,660 | B2 | 3/2004 | Park | 502/304 |
| 6,777,371 | B2 | 8/2004 | Liu | 502/337 |

FOREIGN PATENT DOCUMENTS

| JP | 7-821 | 1/1995 |
|---|---|---|
| JP | 2002-161055 | 6/2005 |

*Primary Examiner*—Elizabeth D. Wood
(74) *Attorney, Agent, or Firm*—Kenneth H. Johnson

(57) ABSTRACT

Improved Ni catalysts for hydrogenation reactions are disclosed. The catalysts are useful for hydrogenation such as selective hydrogenation of acetylenic impurities in crude olefin and diolefin streams. The catalysts are prepared by depositing nickel on a porous support which has the following specific physical properties; BET surface area of from 30 to about 100 $m^2/g$, total nitrogen pore volume of from 0.4 to about 0.9 cc/g, and an average pore diameter of from about 110 to 450 Å with or without modifiers of one or more elements selected from the group consisting of Cu, Re, Pd, Zn, Mg, Mo, Ca and Bi.

1 Claim, 1 Drawing Sheet

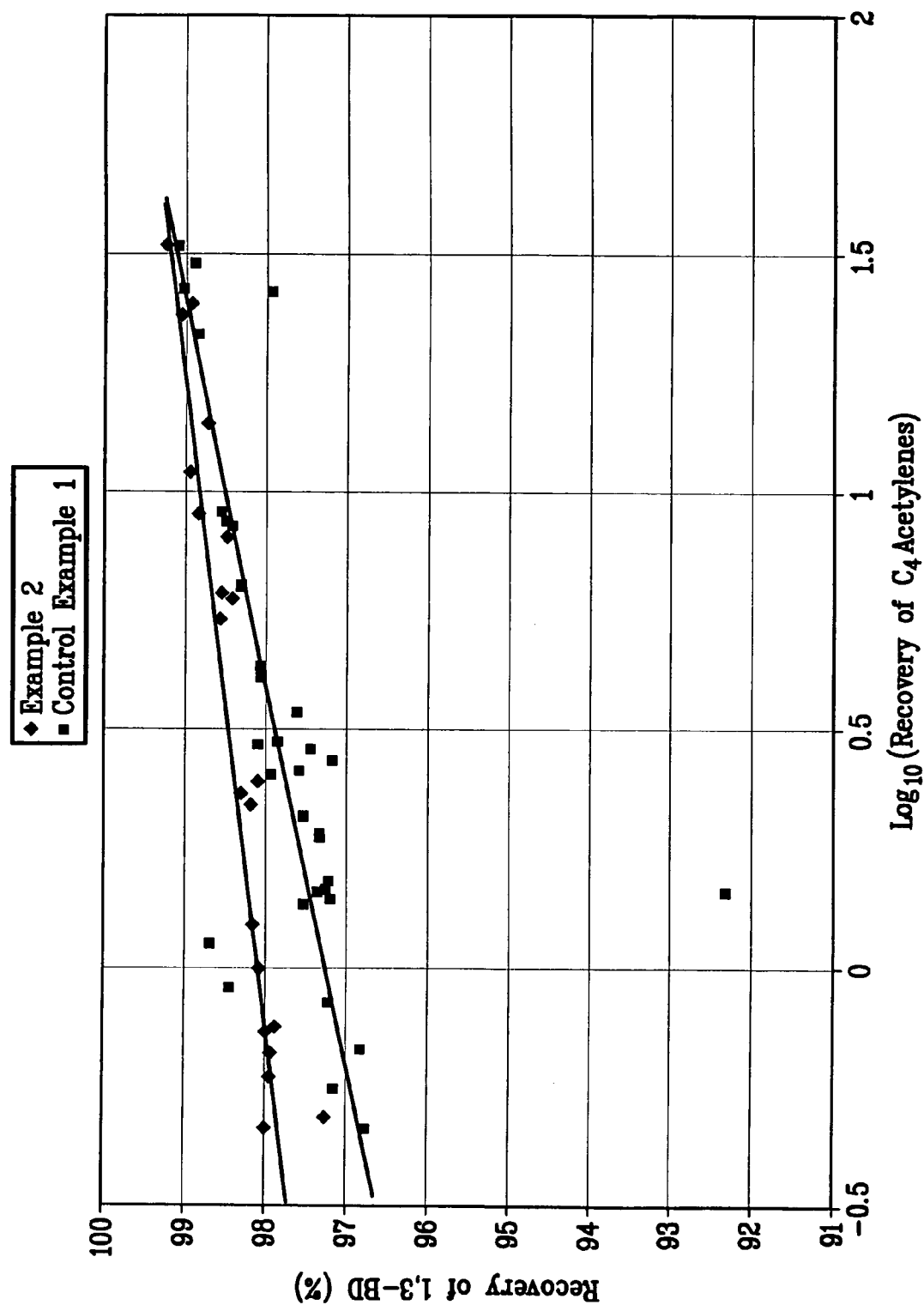

NI HYDROGENATION CATALYSTS, MANUFACTURE AND USE

This is a continuation of Ser. No. 10/633,867, filed on Aug. 4, 2003, now U.S. Pat. No. 7,022,645.

BACKGROUND OF THE INVENTION

Field of the Invention

The present invention relates to new selective hydrogenation catalysts and the method of making the catalysts, which are useful for hydrogenation, such as selective hydrogenation of acetylenic impurities in crude olefin and diolefin streams.

SUMMARY OF THE INVENTION

The present catalysts comprise Ni only or Ni and one or more elements selected from the group consisting of Cu, Re, Pd, Zn, Mg, Mo, Ca and Bi which are deposited on a support having the following physical properties: BET surface area of from 30 to about 100 $m^2/g$, total nitrogen pore volume of from 0.4 to about 0.9 cc/g, and an average pore diameter of from about 110 to 450 Å. Examples of the preferred supports are alumina, silica, zirconia, talcite, silica-alumina, charcoal, etc. The preferred nickel content of the catalyst is from about 4 wt. % to about 20 wt. %.

BRIEF DESCRIPTION OF THE DRAWING

The FIGURE is a graph comparing 1,3-BD recovery of the present selective hydrogenation catalyst to a conventional catalyst.

DETAILED DESCRIPTION OF THE INVENTION

The nickel metal is deposited on a porous support as disclosed by using a conventional impregnation technique such as wet incipient impregnation. The catalyst is useful for selective hydrogenation.

The catalysts comprise Ni only on a support or Ni and one or more elements from Cu, Re, Pd, Zn, Mg, Mo, Ca and Bi to improve the catalyst activity, stability, and the recovery of olefins and diolefins from the crude mixed streams.

Alumina is a preferred support. The preferred alumina is calcined in a temperature range from about 750° to about 1200° C. The preferred calcined alumina in this invention will have at least 30%, preferably at least 50% of the pores larger than 100 Å diameter, and a total pore volume from about 0.4 cc/g to about 0.9 cc/g and ABD (apparent bulk density) from about 0.35 to about 0.75 g/cc. The preferred alumina disclosed in this invention can be prepared by several techniques well known to those skilled in arts preparing active aluminas.

The alumina may contain up to about 2 wt % alkali metal, preferably less than about 2 wt. % alkali metal. One of the preferred aluminas disclosed in this invention can be prepared by the oil dropping gelation technique. The examples of the gelation technique are disclosed in U.S. Pat. No. 2,620,314 (1952), and U.S. Pat. No. 4,273,735 (1981). The spherically shaped alumina may be prepared from aluminum hydroxychloride prepared by digesting aluminum metal in aqueous hydrochloric acid solution. Spherically shaped alumina sol materials, in the form of droplets, are gelled in basic liquid oil phase followed by aging, washing, drying, and calcining to obtain usually gamma-alumina in commercial production at an elevated temperature. Alternatively the preferred spherically shaped alumina also can be prepared by oil dropping gelation technique using the dispersed boehmite or pseudoboehmite alumina sols. See U.S. Pat. No. 4,179,408 (1979). The alumina sols are prepared by dispersing suitable boehmite, pseudoboehmite or mixtures of boehmite and pseudoboehmite aluminas in acidic water. The pseudoboehmite or boehmite raw materials are prepared by hydrolyzing aluminum alkoxides and crystallizing or reacting sodium aluminate with aluminum salts such as aluminum sulfate and crystallizing. Various boehmite alumina or dispersed boehmite alumina sols are available commercially. To prepare the preferred spherical alumina having the pore structure as disclosed in the present invention, Disperal HP 14/2, Dispal 11 N&-80, Dispal 23N4-20, Disperal HP 14, Deperal 40, Pural 200, Pural 100, Pural NG, etc. of mixtures of these may be used. The preferred alumina is transition alumina calcined at an elevated temperature ranging from about 7500 to about 1200° C., producing the delta, kappa, theta and alpha crystalline forms or mixtures thereof. Calcined alumina may contain a minor amount of gamma alumina, if the calcination is carried out at the low end of temperature range defined above.

The preferred alumina in various extrudates or tablet forms can also be prepared by using the preferred boehmite or pseudoboehmite alumina discussed above and calcining at elevated temperatures from about 750° to 1200° C. The surface area of alumina tends to shrink by repeated exposures to elevated temperatures due to slow crystallization to more stable crystal forms: This surface area shrinkage accelerates in the presence of moisture in the atmosphere or trace amounts of sodium in the alumina or both. Usually the prior art alumina support for catalyst preparation is produced as gamma alumina by the calcination at the temperatures from about 550° to 700° C.

The physical shapes of the preferred aluminas in this invention can be any shape such as spheres, extrudates, pellets and granules which preferably have diameters of less than about ¼ inch, preferably ⅛ inch and less than about ½ inch length, and preferably less than ¼ inch length for extrudates or pellets.

Deposition of the nickel on a support can be carried out by single or multiple impregnations. A solution of the nickel compound is prepared by dissolving a nickel compound or an organo nickel compound in organic solvent or water. The examples of the nickel compounds are nickel salts such as nickel nitrate or organo metallic nickel compounds such as nickel acetate, nickel formate, nickel acetylacetonate, nickel alkoxides, etc. The impregnation product is dried and calcined at temperature in a range from 2000 to 600° C., preferably from 2500 to 500° C.

When the present hydrogenation catalysts contain one or more of the elements Cu, Re, Pd, Zn, Mg, Mo, Ca or Bi in addition to Ni, they are preferably employed in the following amounts: Cu— about 0.005 to about 10 wt. %; Re— about 0.1 to about 5 wt. %; Pd— about 0.01 to about 2 wt. %; Zn— about 0.1 to about 10 wt. %; Ca— about 0.1 to about 7 wt. %; Mg— about 0.1 to about 7 wt. %; Mo— about 0.1 to about 10 wt. %; and Bi— about 0.05 to about 7 wt. %.

In the preparation of Bi containing Ni catalyst, the support is preferably impregnated with a solution of bismuth compound before depositing the nickel. An example of a bismuth compound is bismuth nitrate.

When silver containing Ni catalyst is prepared, the support is preferably impregnated with a mixed solution of a nickel compound and silver compound such as silver nitrate.

Optionally a series of sequential impregnations may be carried out starting from the impregnation of the silver compound first on the support.

The evaluation of the catalyst performance is carried out by comparing recovery of a desired product for a given feed stock at a given conversion of acetylenic compounds or at the conversion required to meet specific product qualification against the prior art. For example, when $C_4$ acetylenic compounds in a crude butadiene stream are selectively hydrogenated, 1,3-butadiene is the desired product to be recovered from the feed stream, the following mathematical formula defines the recovery of 1,3-BD.

Recovery of 1,3-$BD$(%)=100−($N_F$−$N_P$)×100/$N_F$ where:
$N_F$=wt. % of 1,3-BD in feed stream, $N_P$=wt. % of 1,3-BD in product stream The recovery of $C_4$ acetylenes (combined vinyl acetylene and ethyl acetylene) is defined in identical manner.

The complete or near complete conversion (less than 30 ppm remains) of $C_4$ acetylenes with high recovery of 1,3-butadiene leads to elimination of one of two extractive distillation units to separate 1,3-butadiene from the mixed stream. The result is a lower production cost of 1,3-butadiene.

The performance of a catalyst deteriorates with on-stream time due to various reasons. One reason is a slow build-up of poisonous carbonaceous materials on the catalyst surface. To prolong the catalyst cycle or service time, a solvent may be used to wash off heavy polymers to slow the build-up rate of the poisonous carbonaceous materials on the catalyst. Therefore, heavy polymers should be soluble, at least some degree, in the solvent under the selective hydrogenation condition. Examples of such solvents are cyclohexane, methyl cyclohexane, benzene, toluene, alkyl nitrites, furfural, dimethyl acetamide, dimethyl formamide, methylpyrrolidone, formylmorpholine, and ethers such as tetrahydrofuran or mixtures thereof. The solvent is recovered from the reactor effluent stream to recycle. Optionally the solvent may be build up in the system, at the start-up of the unit, by recycling heavy components of the feed, which is usually a small part of feed and is also produced by oligomerization and polymerization during the selective hydrogenation in the catalytic reaction zone(s). Solvent is co-fed with the feed to the catalytic reaction zone for the fixed bed operation. For the catalytic distillation or extractive catalytic distillation operation, solvent is introduced at a proper position in the top half of the column. Another alternative operational procedure is occasional washing of the catalysts with solvent at a proper temperature in a range of from 70° F. to 450° F. under a pressure from 0 to 500 psig, preferably in the presence of hydrogen. Another alternative option is that the selective hydrogenation is carried out intermittently in the presence of excess hydrogen in the catalytic reaction zone greater than normally required for a given period of time, for example a few days, even though there is a slightly lower recovery of 1,3-butadiene during this period.

CONTROL EXAMPLE 1

Conventional Catalyst

The commercial Ni catalyst (28 wt % Ni on alumina) was tested to remove $C_4$ acetylenic impurities in a crude feed stream by selective hydrogenation. 40 grams of the catalyst were mixed with 60 ml of 3 mm diameter glass balls and loaded in a vertically mounted up-flow stainless fixed bed reactor (1 inch diameter×20 inch long). The catalyst is 1.2 mm diameter×2–5 mm trilob extrudate. Two thermocouples at each end of catalyst bed were installed to control the reactor temperature. The catalyst was supplied by the manufacturer as an activated and passivated form. The catalyst has the following physical properties; 113 $m^2$/g BET surface area, a total $N_2$ adsorption pore volume of 0.438 $cm^3$/g, and 151 Å average pore diameter. The catalyst was reactivated at 250° F. in 300 cc/min gas flow of 33 volume % hydrogen gas in nitrogen for 1.5 hours and then 575° F. for 5 hours by passing 350 cc per min of pure hydrogen gas. The reactor was cooled to ambient temperature. The selective hydrogenation of acetylenenic impurities in a crude feed steam was carried out at 6 ml/min of hydrocarbon feed and at 44 sccm/min of hydrogen flow rate at the beginning of the reaction down to 21 sccm/min at a constant reactor pressure of 108 psig. The feed comprised 3500 wt ppm $C_4$ acetylenes (2940 ppm VA and 560 ppm EA), 330 ppm methyl acetylene, 66.60 wt % 1,3-BD, 280 wt ppm wt % 1,2-BD, 160 wt ppm propadiene, 21.65 wt % butenes, etc. Because of exothermic heat of hydrogenation, the temperature at the end of the catalyst bed was higher than at the beginning of the catalyst bed. The temperature of the hydrogenation was carried out at a constant temperature of 120° F. The complete conversion of the $C_4$ acetylenes required 44 sccm/min hydrogen or more, at which the recovery of 1,3-BD was 96.8%. The test result is illustrated in the FIGURE. The physical properties of the commercial catalyst are listed in Table 1.

EXAMPLE 2

Invention

A nickel catalyst was prepared to demonstrate a superior catalytic performance of this invention to the conventional Ni catalyst of Example 1 (Control). The catalyst was prepared by carrying out two impregnations. The gamma-alumina used to prepare the nickel catalyst is 1.68 mm diameter spheres prepared by the oil dropping gelation technique. The physical property of the alumina calcined at 750° C. for 3 hour is summarized in Table 1. More than about 95% of the pores in this alumina are larger than 200 Å diameter. The x-ray diffraction (XRD) of this material indicates gamma alumina. After additional calcination at 1100° C. for 3 hour in air, the average diameter of alumina spheres shrunk to 1.45 mm from 1.68 mm. The physical properties of this calcined alumina are listed in Table 1 and used as the support for the Ni. The XRD of this calcined alumina indicates theta alumina with some delta.

A nickel nitrate solution was prepared by dissolving 103 g $NiNO_3.6H_2O$ in 285 grams of water for the first impregnation. 300 grams of the calcined alumina were placed in a rotary impregnator and the nickel nitrate solution was poured on the alumina in the rotary impregnator. After drying the content in the rotary impregnator at about 200° C. by blowing hot air into the rotary impregnator, the dried product was calcined at 350° C. for 2 hours. Another nickel solution was prepared for the second impregnation by dissolving 56 grams $NiNO_3.6H_2O$ in 285 grams in water. The second impregnation was carried out in a similar fashion as the first impregnation. The dried impregnation product was calcined at 380° C. for 2 hours. The amount of nickel deposited on the alumina support is 9.67 wt. % based on the total amount of nickel nitrate used. The physical properties of this Ni catalyst are listed in Table 1.

TABLE 1

|  | SUPPORT 750° C. Cal. | SUPPORT 1100° C. Cal. | 1100° C. Cal. Ni Catalyst | Commercial Ni Catalyst |
|---|---|---|---|---|
| ABD, g/cc | 0.48 | 0.62 | 0.71 | 0.86 |
| BET, $m^2/g$ | 145.0 | 65.6 | 66.0 | 113 |
| Total $N_2$ Pore Volume (cc/g)[†] | 0.925 | 0.713 | 0.626 | 0.438 |
| Average Pore diameter, Å | 216 | 449 | 383 | 151 |

[†]for pores less than 493 Å radius at $P/P_0 = 0.9801$ 40 grams of the catalyst were mixed with 60 ml of 3 mm diameter glass balls and loaded in a vertically mounted up-flow stainless fixed bed reactor (1 inch diameter × 20 inch long). Two thermocouples at each end of catalyst zone were installed to control the reactor temperature. The catalyst was activated at 250° F. in 300 cc/min gas flow of 33 volume % hydrogen gas in nitrogen for 1.5 hours and for 3 hours each at 670° and then 770° F. by passing 350 cc per min of pure hydrogen gas. The reactor was cooled to ambient temperature. The selective hydrogenation of the acetylenic impurities in the same feed used in the Control Example 1 was carried out at 6 ml/min of hydrocarbon feed and 31 sccm/min of hydrogen flow rate at the beginning of the reaction down to 17 sccm/min under a constant reactor pressure of 108 psig and at 120° F. at the end catalyst bed temperature. Because of exothermic heat of hydrogenation, the temperature at the end of the catalyst bed was higher than at the beginning of the catalyst bed.

The complete conversion of the $C_4$ acetylenes required the hydrogen flow rate of 33 sccm/min, at which the recovery of 1,3-BD was 97.7%. The test result is illustrated in the FIGURE. A superior performance of the present catalyst over the performance of the catalyst in the Control Example is clearly demonstrated.

The invention claimed is:

1. A catalyst useful for the selective hydrogenation of acetylenic impurities in crude olefin and diolefin streams consisting of about 9.67 to about 20 wt. % Ni deposited on an alumina support having the following physical properties: BET surface area of from 30 to about 100 $m^2/g$, total nitrogen pore volume of from 0.4 to about 0.9 cc/g, and an average pore diameter of from about 110 to 450, at least 50% of the pores larger than 100 Å diameter, and a total pore volume from about 0.4 cc/g to about 0.9 cc/g and ABD from about 0.35 to about 0.75 g/cc Å.

* * * * *